| United States Patent [19]
Phillippe et al.

[11] Patent Number: 5,141,929
[45] Date of Patent: Aug. 25, 1992

[54] LIPOPHILIC ETHERS AND/OR ESTERS OF D-DESOSAMINE AND THEIR COMPOSITIONS AS ANTI-BACTERIA AND ANTI-FUNGUS AGENTS

[75] Inventors: Michel Phillippe, Antony; Henri Sebag, Paris, both of France

[73] Assignee: Societe Anonyme dite: L'Oreal, Paris, France

[21] Appl. No.: 446,547

[22] Filed: Dec. 6, 1989

[30] Foreign Application Priority Data

Dec. 7, 1988 [FR] France ................ 88 16067

[51] Int. Cl.$^5$ .............. A61K 31/70; C07H 17/00; C07H 5/06; C07H 15/04
[52] U.S. Cl. ........................ 514/62; 514/25; 514/42; 424/DIG. 5; 536/7.2; 536/7.4; 536/17.2; 536/17.9; 536/55.2; 536/115; 536/116; 536/119; 536/120
[58] Field of Search .......... 536/4.1, 7.2, 7.4, 55.2, 536/17.2, 17.9, 115, 116, 120, 119; 514/62, 25, 42; 424/DIG. 5

[56] References Cited

U.S. PATENT DOCUMENTS 2,862,921 12/1958 Booth et al. .................. 536/7.2
3,923,784 12/1975 Kierstead et al. ............. 536/7.4
4,150,220 4/1979 Sciavolino .................... 536/7.4

FOREIGN PATENT DOCUMENTS 2175303 11/1986 United Kingdom .

OTHER PUBLICATIONS

Chemical Abstracts, vol. 79, issued 1973, (Columbus Ohio, U.S.A.), P. Kurath et al., "C-8 Epimeric 8-Hydroxyerythromycins B" see p. 472, column 2, the Abstract No. 92539f Helv. Chim. Acta 1973, 56 (5), 1557-65 (Eng).
Chemical Abstracts, vol. 96, issued 1982, (Columbus Ohio, U.S.A.), H. Redlich et al., "Syntheses of some β-Mycaminose Glycosides", see p. 647, column 1, the Abstract No. 69317h, Liebigs Ann. Chem. 1981, (7), 1223-33 (Ger).
Chemical Abstracts, vol. 110, No. 9, issued 1989, Feb. 27 (Columbus, Ohio, U.S.A.) K. Suzuki et al., "New Glycosidation Reaction 2, Preparation of 1--Fluoro-D-Desosamine Derivative and its Efficient Glycosidation by the use of $C_{p2}HFCl_2$—$AgClO_4$ as the Activator" see page 698, column 1, the Abstract No. 75396h, Tetrahedron Lett. 1988, 29(29), 3571-4 (Eng).
Chemical Abstracts, vol. 113, issued 1990, (Columbus Ohio, U.S.A.) M. Delaforge et al. "In Vivo Effects of Erythromycin, Oleandomycin and Erythralosamine Derivatives on Hepatic Cytochrome P-450", see p. 15, column 2, the Abstract No. 164949u, Biochem. Pharmacol. 1990, 40(2), 223-8 (Eng).
Carbohydrate Research, vol. 1, No. 2, 1965, pp. 137-144, Celmer et al., "The alpha-L- and beta-D-Pyranoside Linkages in Oleandomycin".
Antimicrobial Agents and Chemotherapy, vol. 28, No. 1, Nov. 1985, pp. 630-633, Kibwage et al.: "Antibacterial Activities of Erythromycins A, B, C and D and some of their derivatives".
Chemical Abstracts, vol. 103, No. 7, Aug. 19, 1985, p. 16, No. 47853r Sartori et al.: "Some Erythromycin Derivatives are Strong Inducers in Rats of a Cytochrome P-450 Very similar to that Induced by 16 alpha-Prenenolone Carbonitrile".

Primary Examiner—Johnnie R. Brown
Assistant Examiner—Everett White
Attorney, Agent, or Firm—Cushman, Darby & Cushman

[57] ABSTRACT

Ethers and/or esters of D-desosamine having the formula

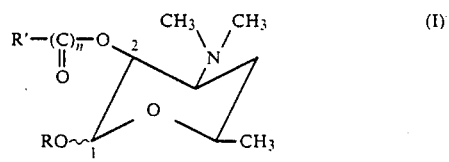

wherein
n represents 0 or 1; R and R', each independently, represent linear or branched alkyl having 1-30 carbon atoms, alkenyl having 5-21 carbon atoms, cycloalkyl having 4-10 carbon atoms, cycloalkylalkyl having 5-11 carbon atoms or phenyl or arylalkyl optionally substituted; or R can represent hydrogen when n=1 and R' can represent hydrogen when n=0, the number of carbon atoms of R, R' or R+R' being equal to 9 to 33 inclusive; or R represents the aglyconic part of erythralosamine and R' represents linear or branched alkyl having 9-30 carbon atoms or alkenyl having 11-21 carbon atoms; and the α and β anomers, their mixture and their salts.

These compounds are usefully employed as anti-bacteria and anti-fungus agents in pharmaceutical and cosmetic compositions.

12 Claims, No Drawings

LIPOPHILIC ETHERS AND/OR ESTERS OF D-DESOSAMINE AND THEIR COMPOSITIONS AS ANTI-BACTERIA AND ANTI-FUNGUS AGENTS

The present invention relates to new lipophilic ethers and/or esters of D-desosamine, to a process for their preparation and to their use as anti-bacteria and anti-fungus agents.

These new ethers and/or esters of D-desosamine are particularly useful in pharmaceutical or cosmetic compositions intended, principally, to combat bacteria proliferation be it of infectious origin or not.

These ethers and/or esters of D-desosamine behave, in effect, in a quite surprising manner, certain ones of them being strong anti-bacteria agents, whereas the same ethers and/or esters of other hydrated carbons, such as glucose or cladinose, exhibit no anti-bacteria activity.

The present invention thus relates to, as new industrial products, lipophilic ethers and/or esters, in position 1 and/or 2, of D-desosamine, which can be represented by the following formula:

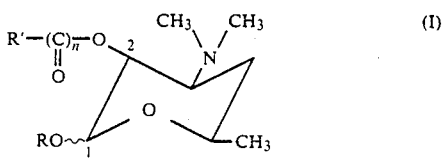

wherein
n represents 0 or 1,

R and R', each independently, represent linear or branched alkyl having 1-30 carbon atoms, alkenyl having 5 to 21 carbon atoms cycloalkyl having 4 to 10 carbon atoms, cycloalkylalkyl having 5 to 11 carbon atoms or phenyl or arylalkyl optionally substituted, R also being able to represent hydrogen when n=1 and R' being able to represent hydrogen when n=0, the number of carbon atoms of R, R' or R+R' ranging between 9 and 33 inclusive, or R represents the aglyconic portion of erythralosamine and R' represents, in this case, a linear or branched alkyl radical having 9 to 30 carbon atoms or an alkenyl radical having 11 to 21 carbon atoms, and the $\alpha$ and $\beta$ anomers and their mixtures as well as the salts of the compounds of formula (I).

Representative linear or branched alkyl radicals having 1 to 30 carbon atoms, include principally, methyl, ethyl, propyl, isopropyl, butyl, tert. butyl, octyl, nonyl, decyl, undecyl, dodecyl, tetradecyl, hexadecyl, octadecyl and 2-decyltetradecyl radicals.

Representative alkenyl radicals having 5 to 21 carbon atoms, include principally undecene-10-yl, heptadecaene-8-yl, heptadecadiene-8,11-yl and heptadecatriene-8,11,14-yl.

The cycloalkyl radical is, preferably, cyclopentyl, cyclohexyl or adamantyl.

Representative substituents on the phenyl radical include halogen, such as chlorine or bromine, OH, trifluoromethyl or lower alkyl having 1-6 carbon atoms.

The arylalkyl radical is preferably benzyl or phenethyl, optionally substituted by the same substituents as those mentioned above for the phenyl radical.

The aglycone of erythralosamine can be represented by the following formula:

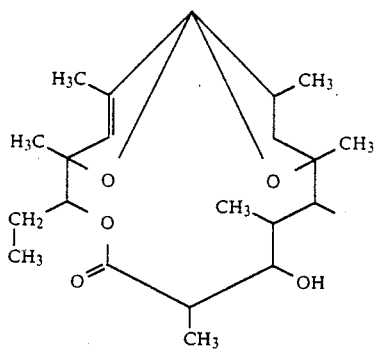

Representative ethers and/or esters of D-desosamine of formula (I) above, include principally the following:

COMPOUND NO.

1. O-decanoyl-2-0-butyl-1-$\alpha$-$\beta$-D-desosamine,
2. O-dodecanoyl-2-0-butyl-1-$\alpha$,$\beta$-D-desosamine,
3. O-dodecanoyl-2-0-butyl-1-$\beta$-D-desosamine,
4. O-dodecanoyl-2-0-methyl-1-$\alpha$,$\beta$-D-desosamine,
5. O-dodecanoyl-2-0-methyl-1-$\alpha$-D-desosamine,
6. O-linoleoyl-2-0-butyl-1-$\alpha$,$\beta$-D-desosamine,
7. O-linoleoyl-2-0-butyl-1-$\alpha$-D-desosamine,
8. O-octadecyl-2-0-butyl-1-$\alpha$,$\beta$-D-desosamine,
9. O-octadecyl-2-0-butyl-1-$\alpha$-D-desosamine,
10. O-octadecyl-2-0-butyl-1-$\beta$-D-desosamine,
11. O-undecyl-2-0-decyl-1-$\alpha$,$\beta$-D-desosamine,
12. O-undecyl-2-0-decyl-1-$\alpha$-D-desosamine,
13. O-undecyl-2-0-decyl-1-$\beta$-D-desosamine,
14. di-O-octyl-1,2-$\alpha$,$\beta$-D-desosamine,
15. di-O-octyl-1,2-$\alpha$-D-desosamine,
16. di-O-octyl-1,2-$\beta$-D-desosamine,
17. O-(2-decyl)-tetradecyl-2-0-butyl -1-$\alpha$,$\beta$-D-desosamine,
18. O-dodecanoyl-2'-erythralosamine,
19. O-oleoyl-2-$\alpha$,$\beta$-D-desosamine,
20. O-decyl-1-$\alpha$,$\beta$-D-desosamine,
21. O-decyl-1-$\alpha$-D-desosamine,
22. O-decyl-1-$\beta$-D-desosamine,
23. O-dodecyl-1-$\alpha$,$\beta$-D-desosamine,
24. O-hexadecyl-1-$\alpha$,$\beta$-D-desosamine and
25. O-(p-nonyl)phenyl-1-$\alpha$,$\beta$-D-desosamine.

In accordance with a particularly preferred embodiment of the present invention, the compounds of formula (I), such as defined above, are esters-ethers respectively in the 2-position and in the 1-position or diethers of which the sum of the carbon atoms of R+R' is between 12 and 30, inclusive. Among the compounds listed above, compounds 1 to 17 respond to this definition.

The present invention also relates to a process for preparing the ethers and/or esters of D-desosamine, such as defined above.

Concerning the preparation of esters, in the 2-position, various esterification procedures can be employed. Preferably, however, the esterification is carried out in an anhydrous organic solvent medium, such as tetrahydrofuran, alone or in admixture with another organic solvent, such as pyridine or N, N-dimethyl formamide, by reacting an excess of the mixed anhydride of the selected acid, prepared in situ, for example, from ethyl chloroformate and the selected acid, on D-desosamine or on a monoether, in position 1, of D-desosamine.

Other esterification procedures can be employed, and principally the method using the imidazolides of the selected acids in an anhydrous solvent, such as pyridine or N, N-dimethyl formamide in the presence of a base such as potassium tert. butanolate or sodium imidazolide. However, these methods generally give lower yields.

The etherification reactions are carried out, for position 1 on D-desosamine, in the presence of a selected alcohol (ROH) and a mineral acid, such as sulfuric acid or hydrochloric acid or an organic acid such as paratoluene sulfuric acid, optionally in an organic solvent such as N,N-dimethyl formamide at a temperature of about 80 degrees C.

The ethers in the 2-position are, preferably, obtained by reacting an R'X halide (X being Cl or Br) or a tosylated derivative on a monoether in position 1 of the D-desosamine, in the presence of a base such as potassium tert. butanolate, in an anhydrous organic solvent, such as dioxane or N,N-dimethyl formamide at a temperature of about 80° C.

The present invention also relates to the use of the ethers and/or esters of D-desosamine, such as defined above, as an anti-bacteria or anti-fungus agent and principally in human and veterinary therapeutic compositions and in cosmetic compositions.

The pharmaceutical compositions can be administered topically, orally, parenterally or rectally and are intended, more particularly, for the treatment of disorders of bacteria origin. The cosmetic compositions are more particularly intended for the treatment of various dermatoses and principally acne. These compositions which are intended for therapeutic or cosmetic treatment can be provided under various forms and, in particular, under anhydrous form. These compositions contain at least one ether and/or ester of D-desosamine, such as defined above, in an amount ranging from 0.001 to 10 percent, and, preferably, from 0.05 to 3 percent by weight relative to the total weight of the composition.

For the preparation of compositions, according to the present invention, containing as the active substance at least one ether and/or ester of D-desosamine, various vehicles and adjuvants, can be employed, which are described in the literature pertaining to pharmacy, cosmetics and related fields.

For the preparation of solutions, a physiologically acceptable organic solvent can be employed.

Representative acceptable organic solvents include acetone, isopropyl alcohol, triglycerides of fatty acids, glycol ethers, $C_1$-$C_4$ alkyl esters of short chain acids, alkyl-ethers of polytetrahydrofuran, as well as volatile silicones such as cyclomethicones.

The compositions according to the present invention can also include thickening agents, such as cellulose and/or cellulose derivatives, in an amount ranging from 0.5 to 20 percent by weight based on the total weight of the composition.

The compositions according to the present invention can also contain, in combination with at least one ether and/or ester of D-desosamine, such as defined above, at least one other antibacteria or anti-fungus agent.

If necessary, a conventional adjuvant selected from the group consisting of anti-oxidants, preservatives, perfumes and dyes can be employed.

Representative anti-oxidants include, for example, tert. butylhydroxyquinone, butylhydroxyanisole, butylhydroxytoluene and α-tocopherol and its derivatives.

The pharmacologic and galenic transformations of the compounds, according to the invention, are effected in a known manner.

The galenic forms can be, for topical application, creams, milks, gels, more or less thick lotions, lotions carried by pads, patches, ointments, sticks or even aerosol formulations provided in the form of sprays or foams.

The compositions for oral administration can be provided in the form of tablets, gelules, lozenges, syrups, suspensions, emulsion, powders, granules or solutions.

The compositions can also be provided in the form of suppositories.

The anti-bacteria and/or anti-fungus treatment, using the topical compositions according to the invention, comprises applying two or three times per day a sufficient amount of the composition on the areas of the skin to be treated for a period Of time ranging from 6 to 30 weeks and preferably from 12 to 24 weeks.

The compositions according to the present invention can also be employed, as a preventive, i.e. on the areas of skin susceptible of being attacked by bacteria proliferation.

Although particular reference has been made to the use of the ethers and/or esters of D-desosamine as active compounds in pharmaceutical and cosmetic compositions, they can also be used as a preservative for such compositions. Further, they find various uses in other fields of industry such as agriculture, paper-making, paints and enamels and in the treatment of water.

COMPARATIVE STUDY OF THE ACTIVITY OF THE LIPOPHILIC ESTERS AND/OR ETHER OF D-DESOSAMINE

The activity of the esters and/or ethers of D-desosamine has been studied by the dilution method to determine the minimum inhibiting concentration (MIC) This method is described and employed by G.A. Denys et al, Antimicrobial Agents and Chemotherapy (1983) 23, 335–337 and J.J. Leyden et al, J. Am. Acad. Dermatol. (1983) 8 (1) 41–5, by using as the *procionibacterium acnes* strain, strain P37 furnished by Cunliffe and Holland.

This P37 strain has been the object of studies described in the following publications:

J. Greenman, K.T. Holland and W.J. Cunliffe, Journal of General Microbiology (1983) 129, 1301–1307;

E. Ingham, K.T. Holland, G. Gowland and W.J. Cunliffe, ibid. (1980) 118, 59–65; and K.T. Holland, J. Greenman and W.J. Cunliffe, Journal of Applied Bacteriology (1979) 47, 383–384.

SELECTION AND ISOLATION OF SENSITIVE AND RESISTANT POPULATIONS

Strain 37 is sensitive to erythromycin as evidenced by its minimum inhibiting concentration (MIC=0.78 μg/ml).

On the other hand, after 8 successive sub-cultures in the same medium (RCM* 19/20, DMSO 19/20 by volume) with the view of obtaining a progressive stabilization of this strain in this medium, a progressive resistance to erythromycin was manifested in the following form:

after spreading a standardized inoculum (DO=1.8 at 450 nm) on a gelose medium (RCM+furazolidone), in a Petri dish, a 9 mm diameter disc is deposited at its center. On the disc, 50 μg of erythromycin (in solution in DMSO) are deposited.

After 6 days at 36° C. in an anerobic medium (GAS-PAK, B.B.L. system) an inhibition zone of the growth of the strain is clearly visible (total diameter=42 mm), the majority of the colonies being situated at the periphery of the inhibition zone.

On the other hand, at the interior of zone few colonies clearly appear.

The two types of colonies are then retained by stripping of the gelose medium (sterilized platinum loop):

(1) at the interior of the inhibition zone there are stripped off strains, called P37 E⊖ by reason of their apparent resistance to erythromycin.

(2) at 1 cm beyond the periphery of the inhibition zone, there are stripped off strains called P37 E⊕.

After isolation and culturing, the P37 E⊕ and P37 E⊖ strains effectively show very different sensitivities to erythromycin as illustrated by the following respective MIC values.

|  | MIC ($\mu$g/ml) |
| --- | --- |
| P37 | 0.78 |
| P37 E⊕ | 0.78 |
| P37 E⊖ | 50 |

*Reinforced Clostridium Medium (OXOID).

This phenomenon is confirmed by the study of the IC 50 (inhibiting concentration at 50%) which represents the concentration of erythromycin where, at a constant culturing time, 50% survivors among the population are found.

|  | IC ($\mu$g/ml) |
| --- | --- |
| P37 | 50 |
| P37 E⊕ | 5 |
| P37 E⊖ | 100 |

The minimum inhibiting concentration (MIC), expressed in $\mu$g/ml of the esters and/or ethers of D-desosamine tested vis-a-vis strains of *propionibacterium Acnes* P37, P37E⊕ and P37E⊖ and *staphilococcus epidermidis* ATCC 12228, is reported in the following Table I.

TABLE I

| Ethers and/or esters of D-desosamine Compound No. (See page 3) | ATCC 12228 | P37 | P37⊕ (sensitive) | P37 E⊖ (resistant) |
| --- | --- | --- | --- | --- |
| 1 | 5 | 9 | 9 | 3.2 |
| 2 | 3.5 | 0.4 | 0.6 | 0.9 |
| 3 | — | 15 | 0.1 | 1.9 |
| 4 | 3.8 | 25 | 15 | 15 |
| 5 | 3.2 | 50 | 50 | 50 |
| 6 | 0.2 | 0.4 | 0.7 | 0.8 |
| 7 | 1.1 | 0.15 | 1.1 | 1.1 |
| 8 | 2.2 | 0.25 | <0.03 | 8.8 |
| 9 | 0.8 | 0.1 | 27.5 | 27.5 |
| 10 | 0.04 | 3.12 | 0.09 | 1.56 |
| 11 | 0.7 | 4 | 0.7 | 0.8 |
| 12 | 0.8 | 1.8 | 1 | 0.8 |
| 13 | 0.06 | 1 | 0.5 | 0.02 |
| 14 | 0.5 | 0.5 | 0.6 | 0.1 |
| 15 | 0.3 | 1.8 | 1 | 0.4 |
| 16 | 1.2 | 0.7 | 0.3 | 0.15 |
| 17 | — | 12.5 | 11 | 6 |
| 18 | 1.5 | 0.4 | 12.5 | 0.4 |

EXAMPLES OF PREPARATION

EXAMPLE 1

Preparation of O-decanoyl-2-O-butyl-1-$\alpha$,$\beta$-D-desosamine

In a round bottom flask, under an inert atmosphere, 2.8 g (16.6 mmoles) of decanoic acid are dissolved in 50 ml of anhydrous tetrahydrofuran; the reaction mixture is cooled to 0° C. 3 ml of anhydrous pyridine and 1.6 ml (16.6 mmoles) of ethyl chloroformate are added thereto. The solution is stirred for 5 minutes and 2.5 g of sodium bicarbonate are added. Thereafter, 1.5 g (6.5 mmoles) of O-butyl-$\alpha$,$\beta$-D-desosamine, previously dissolved in 70 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is chromatographed on a silica gel column (H.P.L.C.) by using, as the eluant: ethyl acetate (4)/hexane (6) thereby resulting in the isolation of 1.8 g (72% yield) of O-decanoyl-2-O-butyl-1-$\alpha$,$\beta$-D-desosamine.

Microanalysis: $C_{22}H_{43}NO_4.1H_2O$; M=394.6.

|  | C | H |
| --- | --- | --- |
| Calculated, % | 66.96 | 11.24 |
| Found, % | 67.49 | 11.20 |

The NMR of $^{13}C$ (CDCl$_3$, ref. int. T.M.S.) confirms the esterification of the anomers $\alpha$ and $\beta$ in position 2 of the desosamine ring.

EXAMPLE 2

Preparation of O-dodecanoyl-2-O-butyl-1-$\alpha$,$\beta$-D-desosamine

In a round bottom flask, under an inert atmosphere, 3.35 g (16.7 mmoles) of dodecanoic acid are dissolved in 45 ml of anhydrous tetrahydrofuran; the reaction mixture is cooled to 0° C. and then poured into 3 ml (38 mmoles) of anhydrous pyridine and 1.6 ml (16.6 moles) of ethyl chloroformate. The solution is stirred for 5 minutes and 2.5 g (30 mmoles) of sodium bicarbonate are added. Thereafter, 1.5 g (6.5 mmoles) of O-butyl-$\alpha$,$\beta$-D-desosamine previously dissolved in 100 ml of tetrahydrofuran are added. The reaction mixture is then stirred for 10 hours while permitting the temperature thereof to return to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under partial vacuum. The resulting crude product is chromatographed on a silica gel column (H.P.L.C.) using as the eluant: ethyl acetate (4)/hexane (6) thereby resulting in the isolation of 2.2 g (82% yield) of O-dodecanoyl-2-O-butyl-1-$\alpha$,$\beta$-D-desosamine.

Microanalysis: $C_{24}H_{47}NO_4$; M=413.65

|  | C | H | N |
| --- | --- | --- | --- |
| Calc. % | 69.69 | 11.45 | 3.39 |
| Found % | 69.59 | 11.40 | 3.24 |

-continued

| | C | H | N |
|---|---|---|---|
| NMR of $^{13}$C (CDCl$_3$, ref. int. T.M.S.) | | | |

The negative γ effects in 1 (−3.3 ppm and −2.5 ppm respectively for the α and β anomers) as well as in 3 (−2.8 ppm and −1.8 ppm for the α and β anomers) show the esterification in position 2.

EXAMPLE 3

Preparation of O-dodecanoyl-2-O-butyl-1-β-D-desosamine

In a round bottom flask, under an inert atmosphere, 3.35 g (16.7 mmoles) of dodecanoic acid are dissolved in 45 ml of anhydrous tetrahydrofuran: the reaction mixture is cooled to 0° C. and then poured into 3 ml of anhydrous pyridine and 1.6 ml (16.6 mmoles) of ethyl chloroformate. The solution is stirred for 5 minutes and 2.5 g of sodium bicarbonate are added. Thereafter 1.5 g (6.5 mmoles) of O-butyl-β-D-desosamine, previously dissolved in 100 ml of tetrahydrofuran are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is chromatographed on a silica gel column (H.P.L.C.) using as the eluant: ethyl acetate (4)/hexane (6) thereby resulting in the isolation of 2 g (75% yield) of pure O-dodecanoyl-2-O-butyl-1-β-D-desosamine.

Microanalysis: $C_{24}H_{47}NO_4$; M=413.65.

| | C | H | N |
|---|---|---|---|
| Calc. % | 69.69 | 11.45 | 3.39 |
| Found % | 69.04 | 11.89 | 2.96 |

$[\alpha]_D^{20} = +19°$ (C=0.5 mg/ml, dichloromethane).
NMR of $^{13}$C (CDCl$_3$, ref. int. T.M.S.).

Negative γ effects in 1 (−2.7 ppm) and 3(−2.3 ppm) indicate the position of the ester in the 2-position.

EXAMPLE 4

Preparation of O-dodecanoyl-2-O-methyl-1-α,β-D-desosamine

This compound is prepared in accordance with the same procedures as those described in Example 1 from O-methyl-1-α,β-D-desosamine - yield 68%.
Microanalysis: $C_{21}H_{41}NO_4$; M=371.6

| | C | H |
|---|---|---|
| Calc. % | 69.88 | 11.12 |
| Found % | 67.65 | 11.08 |

The NMR $^1$H (CDCl$_3$, ref. int. T.M.S.) confirms the expected structure.

EXAMPLE 5

Preparation of O-dodecanoyl-2-O-methyl-1-α-D-desosamine

This compound is prepared in accordance with the same procedures as those described in Example 1 from O-methyl-1-α,β-D-desosamine and purification of the anomeric mixture (45% yield).
Microanalysis: $C_{21}H_{41}NO_4$; M=371.6

| | C | H |
|---|---|---|
| Calc. % | 67.88 | 11.12 |
| Found % | 67.99 | 11.18 |

The NMR $^1$H (CDCl$_3$, ref. int. T.M.S.) confirms the expected structure.

EXAMPLE 6

Preparation of O-linoleoyl-2-O-butyl-1-α,β-D-desosamine

This compound is prepared in accordance with the same procedures as those described in Example 1 from O-butyl-1-α,β-D-desosamine (70% yield).
Microanalysis: $C_{30}H_{55}NO_4 \cdot 0.5H_2O$; M=502.8.

| | C | H | N |
|---|---|---|---|
| Calc. % | 71.66 | 11.22 | 2.78 |
| Found % | 71.91 | 11.06 | 2.77 |

NMR $^1$H (CDCl$_3$, ref. int. T.M.S.) confirms the expected structure.

EXAMPLE 7

Preparation of O-linoleoyl-2-O-butyl-1-α-D-desosamine

This compound is prepared in accordance with the same procedures as those described in Example 1 from O-butyl-1-α,β-D-desosamine and purification of the anomeric mixture (45% yield).
$[\alpha]_D^{20} = +71°$ (C=0.85 mg/ml, dichloromethane).
Microanalysis: $C_{30}H_{55}NO_4$; M=493.8.

| | C | H | N |
|---|---|---|---|
| Calc. % | 72.97 | 11.23 | 2.84 |
| Found % | 72.38 | 11.00 | 2.85 |

NMR of $^{13}$C (CDCl$_3$, ref. int. T.M.S.): The negative γ effects in 1 (−2.3 ppm) and 3 (−1.7 ppm) show the esterification in position 2 and the anomeric position in α.

EXAMPLE 8

Preparation of O-oleoyl-2-α,β-D-desosamine

This compound is prepared in accordance with the same procedures as those described in Example 1 from α,β-D-desosamine (50% yield).
Microanalysis: $C_{26}H_{49}NO_4 \cdot 0.5H_2O$; M=448.7.

| | C | H | N |
|---|---|---|---|
| Calc. % | 69.59 | 11.23 | 3.12 |
| Found % | 69.57 | 11.11 | 3.12 |

NMR of $^{13}$C (CDCl$_3$, ref. int. T.M.S.): The chemical displacements of the $C_1\alpha$ (90.78 ppm) and $C_1\beta$ (96.68 ppm), $C_2\alpha$ (70.93 ppm) and $C_2\beta$ (72.78 ppm) show the esterification in the 2 position.
NMR $^1$H (CDCl$_3$, ref. int. T.M.S.): the chemical displacements and couplings of the H$_1$ (H$_1$ of the anomer β:δ:4.46 ppm-J=7.6 Hz; H₁ of the anomer α:δ:5.21 ppm-J=3.3 Hz) confirms the α,β anomeric mixture with esterification in the 2 position.

EXAMPLE 9

Preparation of O-dodecanoyl-2'-erythralosamine

This compound is prepared in accordance with the same procedures as those described in Example 1 from erythralosamine (65% yield) $[\alpha]_D^{20} = +0.29°$ (C=3 mg/ml, dichloromethane).

Microanalysis: $C_{41}H_{71}NO_9$; M=722,

|  | C | H | N |
|---|---|---|---|
| Calc. % | 68.20 | 9.91 | 1.94 |
| Found % | 67.78 | 9.96 | 1.94 |

The NMR of $^{13}C$ confirms the expected structure (CDCl₃, ref. int. T.M.S.).

EXAMPLE 10

Preparation of O-decyl-1-α,β-D-desosamine

In a round bottom flask fitted with a condenser, 3 g (17 mmoles) of D-desosamine are dissolved in 30 ml of decanol. 2 ml of 95% sulfuric acid are then added and the reaction is carried out at 70° C. for 10 hours (CCM: dichloromethane/15% methanol). The reaction medium is then extracted (dichloromethane/bicarbonated water). The organic phase is washed and then dried on sodium sulfate to give 4.5 g (83% yield) of O-decyl-1-α,β-D-desosamine.

Microanalysis: $C_{18}H_{37}NO_3$; M=315.5,

|  | C | H | N |
|---|---|---|---|
| Calc. % | 68.53 | 11.82 | 4.44 |
| Found % | 68.38 | 11.71 | 4.27 |

NMR of $^{13}C$ (CDCl₃, ref. int. T.M.S.): the chemical displacements of the C₁α (98.53 ppm) and C₁β 103.2 ppm), show the esterification in position 1.

EXAMPLE 11

Preparation of O-decyl-1-α-D-desosamine

This compound is isolated by the H.P.L.C. purification (dichloromethane/8% methanol) of the anomeric mixture described in Example 10.

Microanalysis: $C_{18}H_{37}NO_3$; M=315.5.

|  | C | H | N |
|---|---|---|---|
| Calc. % | 68.53 | 11.82 | 4.40 |
| Found % | 68.20 | 11.46 | 4.16 |

The NMR of $^1H$ (CDCl₃, ref. int. T.M.S.) confirms the expected structure.

EXAMPLE 12

Preparation of O-decyl-1-β-D-desosamine

This compound is isolated by H.P.L.C. purification (dichloromethane/8% methanol) of the anomeric mixture described in Example 10.

Microanalysis: $C_{18}H_{37}NO_3 \cdot 0.5H_2O$; M=324.5.

|  | C | H | N |
|---|---|---|---|
| Calc. % | 66.62 | 11.82 | 4.32 |
| Found % | 66.03 | 11.94 | 4.64 |

The NMR of $^1H$ (CDCl₃, ref. int. T.M.S.) confirms the expected structure.

EXAMPLE 13

Preparation of O-dodecyl-1-α,β-D-desosamine

This compound was synthesized in accordance with the procedures described in Example 10 from D-desosamine and dodecanol (85% yield).

Microanalysis: $C_{20}H_{41}NO_3 \cdot 0.75H_2O$; M=357.1.

|  | C | H | N |
|---|---|---|---|
| Calc. % | 67.26 | 11.98 | 3.92 |
| Found % | 67.37 | 12.09 | 3.82 |

The NMR of $^1H$ (CDCl₃, ref. int. T.M.S.) confirms the expected structure.

EXAMPLE 14

Preparation of O-hexadecyl-1-α,β-D-desosamine

This compound was synthesized in accordance with the procedure described in Example 10 from D-desosamine and hexadecanol (85% yield).

Microanalysis: $C_{24}H_{49}NO_3$; M=399.7.

|  | C | H | N |
|---|---|---|---|
| Calc. | 72.12 | 12.36 | 3.50 |
| Found % | 71.60 | 12.24 | 3.44 |

NMR of $^{13}C$ (CDCl₃, ref. int. T.M.S.): the chemical displacements of the C₁β (103.75 ppm), C₁α (98.27 ppm), C₂β (69.71 ppm) and C₂α (68.43 ppm) are in agreement with the proposed formula.

The NMR of $^1H$ (CDCl₃, ref. int. T.M.S.) confirms this structure.

EXAMPLE 15

Preparation of O-octadecyl-2-O-butyl-1-α,β-D-desosamine

In a round bottom flask fitted with a condenser, under an inert atmosphere, 4 g (17 mmoles) of O-butyl-1-α,β-D-desosamine are dissolved in 150 ml of anhydrous N,N-dimethylformamide. 3.9 g (34 mmoles) of potassium tert. butanolate are added and the entire mixture is stirred at ambient temperature for 45 minutes. 11.5 g (34 mmoles) of bromooctadecane are then added. The reaction mixture is then stirred for 12 hours at 100° C. The mixture is then extracted (ethyl acetate/water) and the organic phase washed and dried on magnesium sulfate. After evaporation of the solvents, the crude product is chromatographed on a silica gel column (ethylacetate (5)/heptane(5)) thereby providing 7 g (83% yield) of O-octadecyl-2-O-butyl-1-α,β-D-desosamine.

Microanalysis: $C_{30}H_{61}NO_3 \cdot 0.5H_2O$; M=492.8.

|  | C | H | N |
|---|---|---|---|
| Calc. % | 73.11 | 12.68 | 2.84 |

-continued

| | C | H | N |
|---|---|---|---|
| Found % | 73.13 | 12.79 | 2.84 |

The NMR of $^1$H (CDCl$_3$, ref. int. T.M.S.) confirms the expected structure.

EXAMPLE 16

Preparation of O-octadecyl-2-O-butyl-1-α-D-desosamine

This compound was isolated by H.P.L.C. purification of the anomeric mixture described in Example 15 (ethylacetate (5)/heptane (5)).

$[\alpha]_D^{20} = +79°$ (C=0.6 mg/ml, dichloromethane).
Microanalysis: C$_{30}$H$_{61}$NO$_3$; M=483.8.

| | C | H | N |
|---|---|---|---|
| Calc. % | 74.48 | 12.71 | 2.90 |
| Found % | 73.98 | 12.74 | 2.88 |

The NMR $^1$H structure (CDCl$_3$, ref. int. T.M.S.) confirms the expected structure.

EXAMPLE 17

Preparation of O-octadecyl-2-O-butyl-1-β-D-desosamine

This compound was isolated by H.P.L.C. purification (ethyl acetate (5)/heptane (5)) of the anomeric mixture described in Example 15.

$[\alpha]_D^{20} = -15°$ (0.4 mg/ml, dichloromethane).
Microanalysis: C$_{30}$H$_{61}$NO$_3$·0.5H$_2$O; M=492.8.

| | C | H | N |
|---|---|---|---|
| Calc. % | 73.11 | 12.68 | 2.84 |
| Found % | 73.70 | 12.74 | 2.79 |

NMR of $^{13}$C (CDCl$_3$, ref. int. T.M.S.): the chemical displacements of C$_1$ (104.9 ppm) and C$_3$ (63.95 ppm) indicate both the anomerization in β and the etherification by the C$_{18}$ chain in position 2.

EXAMPLE 18

Preparation of O-undecyl-2-O-decyl-1-α,β-D-desosamine

This compound was prepared for O-decyl-1-α,β-D-desosamine and 1-bromo undecane in accordance with the procedure described in Example 15 (72% yield).
Microanalysis: C$_{29}$H$_{59}$NO$_3$; M=469.8.

| | C | H | N |
|---|---|---|---|
| Calc. % | 74.14 | 12.66 | 2.98 |
| Found % | 74.07 | 12.62 | 2.89 |

The NMR of $^{13}$C (CDCl$_3$, ref. int. T.M.S.): the chemical displacements of C$_1\alpha$ (96.60 ppm) and C$_1\beta$ (105.01 ppm) show the etherification at position 1.

EXAMPLE 19

Preparation of O-undecyl-2-O-decyl-1-α-D-desosamine

This compound was isolated by H.P.L.C. purification (ethyl acetate (5)/heptane (5)) of the anomeric mixture described in Example 18.

$[\alpha]_D^{20} = +66°$ (C=1.4 mg/ml, dichloromethane).
Microanalysis: C$_{29}$H$_{59}$NO$_3$; M=469.8.

| | C | H · | N |
|---|---|---|---|
| Calc. % | 74.14 | 12.66 | 2.98 |
| Found % | 74.04 | 12.68 | 2.97 |

The NMR of $^1$H (CDCl$_3$, ref. int. T.M.S.) confirms the expected structure.

EXAMPLE 20

Preparation of O-undecyl-2-O-decyl-1-β-D-desosamine

This compound was isolated by H.P.L.C. purification (ethyl acetate (5)/heptane (5)) of the anomeric mixture described in Example 18.

$[\alpha]_D^{20} = -18°$ (C=1.7 mg/ml, dichloromethane).
Microanalysis: C$_{29}$H$_{59}$NO$_3$; M=469.8.

| | C | H | N |
|---|---|---|---|
| Calc. % | 74.14 | 12.66 | 2.98 |
| Found % | 74.25 | 12.55 | 2.72 |

The NMR of $^1$H (CDCl$_3$, ref. int. T.M.S.) confirms the expected structure.

EXAMPLE 24

Preparation of di-O-octyl-1,2-α,β-D-desosamine

This compound was prepared from octyl-1-α,β-D-desosamine and 1-bromo octane in accordance with the procedure described in Example 15 (70% yield).
Microanalysis: C$_{24}$H$_{49}$NO$_3$; M=399.7.

| | C | H | N |
|---|---|---|---|
| Calc. % | 72.13 | 12.36 | 3.50 |
| Found % | 71.62 | 12.51 | 3.44 |

The NMR of $^1$H (CDCl$_3$, ref. int. T.M.S.) confirms the expected structure.

EXAMPLE 22

Preparation of di-O-octyl-1,2-α-D-desosamine

This compound was isolated by H.P.L.C. purification (ethyl acetate (5)/heptane (5)) of the anomeric mixture described in Example 21.
Microanalysis: C$_{24}$H$_{49}$NO$_3$; M=399.7.

| | C | H | N |
|---|---|---|---|
| Calc. % | 72.13 | 12.36 | 3.50 |
| Found % | 71.88 | 12.33 | 3.52 |

The NMR of $^1$H (CDCl$_3$, ref. int. T.M.S.) confirms the expected structure.

EXAMPLE 23

Preparation of di-O-octyl-1,2-β-D-desosamine

This compound was isolated by H.P.L.C. purification (ethyl acetate (5)/heptane (5)) of the anomeric mixture described in Example 21.
Microanalysis: C$_{24}$H$_{49}$NO$_3$; M=399.7.

| | C | H | N |
|---|---|---|---|
| Calc. % | 72.13 | 12.36 | 3.50 |
| Found % | 72.12 | 12.35 | 3.55 |

The NMR of $^{13}C$ (CDCl$_3$, ref. int. T.M.S.) shows by the chemical displacement of $C_1$ at 104.98 ppm that the anomer is $\beta$.

EXAMPLE 24

Preparation of O-(2-decyl)-tetradecyl-2-O-butyl-1-$\alpha,\beta$-D-desosamine

This compound was prepared from O-decyl-2-O-tosyl-1-tetradecanol and O-butyl-1-$\alpha,\beta$-D-desosamine in accordance with the procedure described in Example 15 (72% yield).

Microanalysis: $C_{36}H_{73}NO_3$; M=568.

| | C | H | N |
|---|---|---|---|
| Calc. % | 76.12 | 12.95 | 2.46 |
| Found % | 76.36 | 12.78 | 2.09 |

The NMR of $^1H$ (CDCl$_3$, ref. int. T.M.S.) confirms the expected structure.

EXAMPLE 25

Preparation of O-(p-nonyl) phenyl-1-$\alpha,\beta$-D-desosamine

This compound was prepared from p-nonylphenol and D-desosamine in accordance with the procedure described in Example 10 (60% yield).

Microanalysis: $C_{23}H_{39}NO_3 \cdot 0.5H_2O$; M=386.6.

| | C | H | N |
|---|---|---|---|
| Calc. % | 71.45 | 10.42 | 3.62 |
| Found % | 71.46 | 10.51 | 3.15 |

The NMR of $^1H$ (CDCl$_3$, ref. int. T.M.S.) confirms the expected structure.

PHARMACEUTICAL AND COSMETIC COMPOSITIONS

We claim:

1. A compound comprising the ether, ester or ester-ether of D-desosamine having the formula

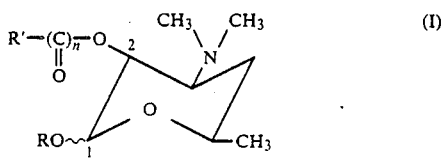

wherein
n represents 0 or 1,
R and R', each independently, represent linear or branched alkyl having 1–30 carbon atoms, alkenyl having 5–21 carbon atoms, cycloalkyl having 4–10 carbon atoms, cycloalkylalkyl having 5-11 carbon atoms, phenyl or arylalkyl, or
R can also represent hydrogen when n=1 and R' can represent hydrogen when n=0,
the number of carbon atoms of R+R' being between 9 and 33 inclusive, or
R represents the aglyconic portion of erythralosamine having the formula

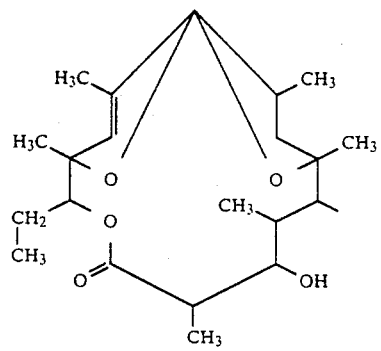

and R', in this case, represents linear or branched alkyl having 9–30 carbon atoms or alkenyl having 11–21 carbon atoms, and
the $\alpha$ and $\beta$ anomers thereof, their mixtures and their salts.

2. The compound of claim 1 wherein said linear or branched alkyl having 1–30 carbon atoms is methyl, ethyl, propyl, isopropyl, butyl, tert. butyl, octyl, nonyl, decyl, undecyl, dodecyl, tetradecyl, hexadecyl, octadecyl or 2-decyl tetradecyl.

3. The compound of claim 1 wherein said alkenyl having 5–21 carbon atoms is undecene-10-yl, heptadecaene-8-yl, heptadecadiene-8,11-yl or heptadecatriene-8,11,14-yl.

4. The compound of claim 1 wherein said cycloalkyl is cyclopentyl, cyclohexyl or adamantyl.

5. The compound of claim 1 wherein said phenyl is substituted by chlorine, bromine, OH, trifluoromethyl or lower alkyl.

6. The compound of claim 1 wherein said arylalkyl is benzyl or phenylethyl.

7. The compound according to the claim 6 wherein said benzyl or phenylethyl is substituted by chlorine, bromine, OH, trifluoromethyl or lower alkyl.

8. The compound of claim 1 selected from the group consisting of:
O-decanoyl-2-0-butyl-1-$\alpha,\beta$-D-desosamine,
O-dodecanoyl-2-0-butyl-1-$\alpha,\beta$-D-desosamine,
O-dodecanoyl-2-0-butyl-1-$\beta$-D-desosamine,
O-dodecanoyl-2-0-methyl-1-$\alpha,\beta$-D-desosamine,
O-dodecanoyl-2-0-methyl-1-$\alpha$-D-desosamine,
O-linoleoyl-2-0-butyl-1-$\alpha,\beta$-D-desosamine,
O-linoleoyl-2-0-butyl-1-$\alpha$-D-desosamine,
O-octadecyl-2-0-butyl-1-$\alpha,\beta$-D-desosamine,
O-octadecyl-2-0-butyl-1-$\alpha$-D-desosamine,
O-octadecyl-2-0-butyl-1-$\beta$-D-desosamine,
O-undecyl-2-0-decyl-1-$\alpha,\beta$-D-desosamine,
O-undecyl-2-0-decyl-1-$\alpha$-D-desosamine,
O-undecyl-2-0-decyl-1-$\beta$-D-desosamine,
di-O-octyl-1,2-$\alpha,\beta$-D-desosamine,
di-O-octyl-1,2-$\alpha$-D-desosamine,
di-O-octyl-1,2-$\beta$-D-desosamine,
O-(2-decyl)-tetradecyl-2-0-butyl-1,2-$\alpha,\beta$-D-desosamine,
O-dodecanoyl-2'-erythralosamine,
O-oleoyl-2-$\alpha,\beta$-D-desosamine,
O-decyl-1-$\alpha,\beta$-D-desosamine,
O-decyl-1-$\alpha$-D-desosamine,
O-decyl-1-$\beta$-D-desosamine,
O-dodecyl-1-$\alpha,\beta$-D-desosamine, O-hexadecyl-1-α,β-D-desosamine and
O-(p-nonyl)phenyl-1-α,β-D-desosamine.

9. The compound of claim 1 being esters - ethers respectively in position 2 and position 1 or diethers, the sum of the carbon atoms of R+R' being between 12 and 30 inclusive.

10. A composition for pharmaceutical or cosmetic use comprising in a vehicle appropriate for said pharmaceutical or cosmetic use the compound of claim 1 in an amount effective to combat against fungus or bacteria proliferation.

11. The composition of claim 10 wherein said compound is present in an amount ranging from 0.001 to 5 percent by weight based on the total weight of said composition.

12. The composition of claim 10 wherein said compound is present in an amount ranging from 0.05 to 3 percent by weight based on the total weight of said composition.

* * * * *

UNITED STATES PATENT AND TRADEMARK OFFICE
CERTIFICATE OF CORRECTION

PATENT NO. : 5,141,929

DATED : August 25, 1992

INVENTOR(S) : PHILIPPE et al

It is certified that error appears in the above-identified patent and that said Letters Patent is hereby corrected as shown below:

On the title page: ITEM

[19], "Phillippe et al." should read --Philippe et al--.

[75], "Michel Phillippe" should read --Michel Philippe--.

Signed and Sealed this

Fifth Day of October, 1993

*Attest:*

BRUCE LEHMAN

*Attesting Officer*  *Commissioner of Patents and Trademarks*